United States Patent [19]

Brown

[11] Patent Number: 4,711,233
[45] Date of Patent: Dec. 8, 1987

[54] METHOD AND APPARATUS FOR CEMENTING AN ACETABULAR CUP TO AN ACETABULUM

[76] Inventor: Byron L. Brown, 2315 Hendricks, Fort Smith, Ark. 72903

[21] Appl. No.: 748,856

[22] Filed: Jun. 26, 1985

[51] Int. Cl.$^4$ ............................................. A61F 5/04
[52] U.S. Cl. ............................ 128/92 VP; 128/92 VQ
[58] Field of Search .............. 128/92 R, 92 V, 92 VP, 128/92 VQ

[56] References Cited

U.S. PATENT DOCUMENTS

| | | | |
|---|---|---|---|
| 3,889,665 | 6/1975 | Ling et al. | 128/92 VP |
| 3,924,274 | 12/1975 | Heimke et al. | 128/92 VP |
| 4,271,849 | 6/1981 | Rehder | 128/92 V |
| 4,274,163 | 6/1981 | Malcom et al. | 128/92 VO |
| 4,285,071 | 8/1981 | Nelson et al. | 128/92 VP |
| 4,399,814 | 8/1983 | Pratt, Jr. et al. | 128/92 R |
| 4,462,394 | 7/1984 | Jacobs | 128/92 VP |
| 4,488,549 | 12/1984 | Lee et al. | 128/92 VP |
| 4,528,980 | 7/1985 | Kenna | 128/92 VP |
| 4,595,006 | 6/1986 | Burke et al. | 128/92 VQ |

OTHER PUBLICATIONS

Zimmer, "Charnley-Type Totalhip", pp. A40, A45 of the Product Catalog for 1978.
Add page "The Well Dressed Wound Wears Cover-Strip Wound Closure Strips" by Beiersdorf Inc. of Norwalk, CT.
3M Brochure SD-QAMB (102.5) II entitled "The Closure with Clout", from Surgical Products Division/3M, St. Paul, MN undated.

Primary Examiner—C. Fred Rosenbaum
Assistant Examiner—C. W. Shedd
Attorney, Agent, or Firm—Sigalos & Levine

[57] ABSTRACT

A method and apparatus for attaching an acetabular cup to an acetabulum wherein the cup is rigidly attached to the acetabulum in a spaced relationship and the space between the cup and the acetabulum is filled with a flowable cement under pressure whereby a portion of the medullary bone is partially filled with cement and that pressure maintained until the flowable cement hardens thereby retaining the cup in the acetabulum in a fixed relationship.

33 Claims, 23 Drawing Figures

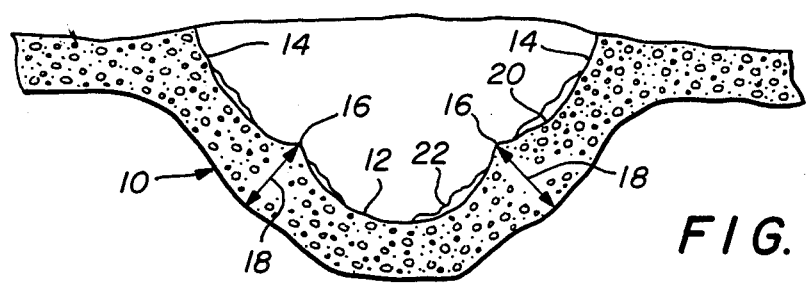
FIG. IA
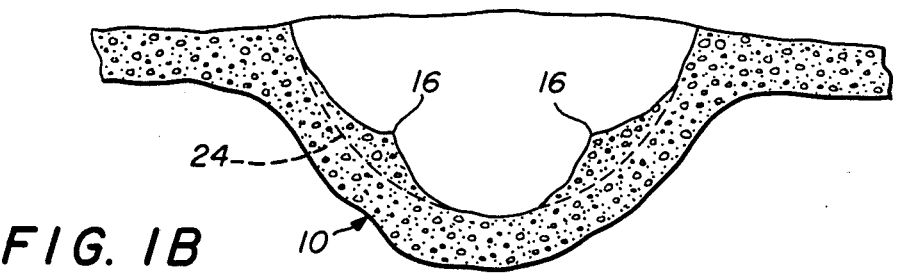
FIG. IB
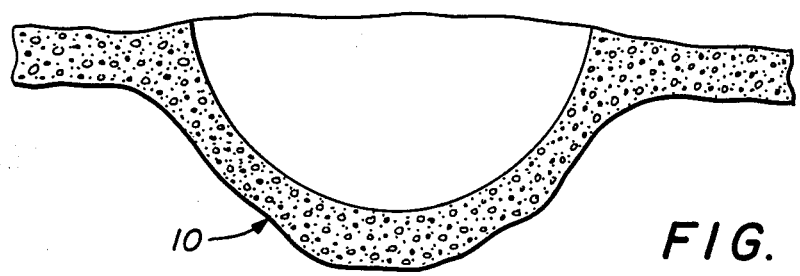
FIG. IC
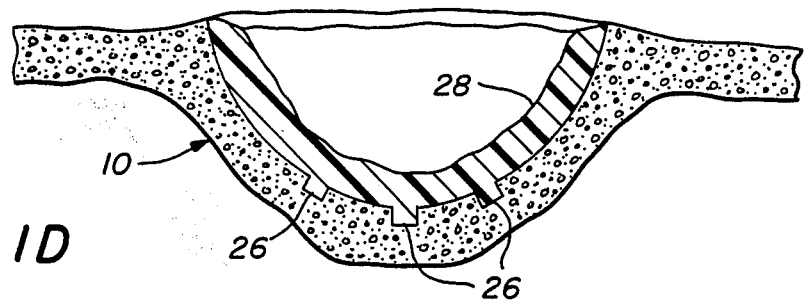
FIG. ID
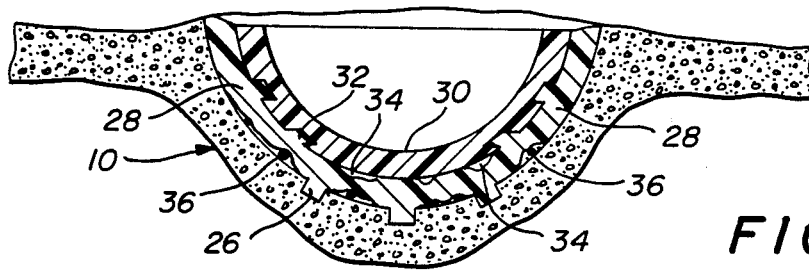
FIG. IE

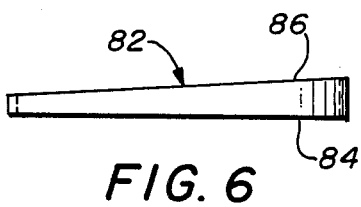
FIG. 6
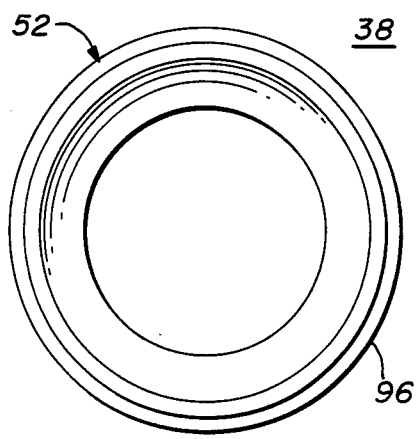
FIG. 7A
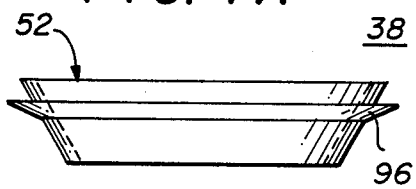
FIG. 7B
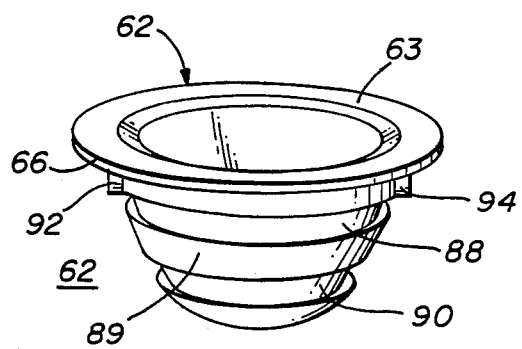
FIG. 8A
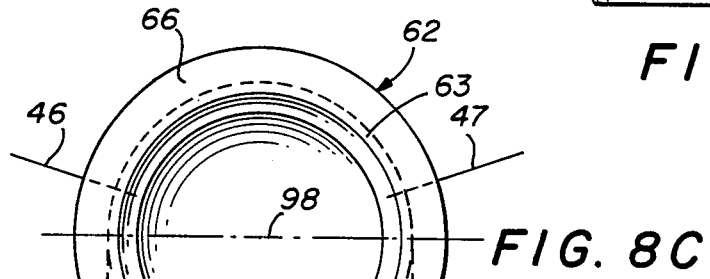
FIG. 8C
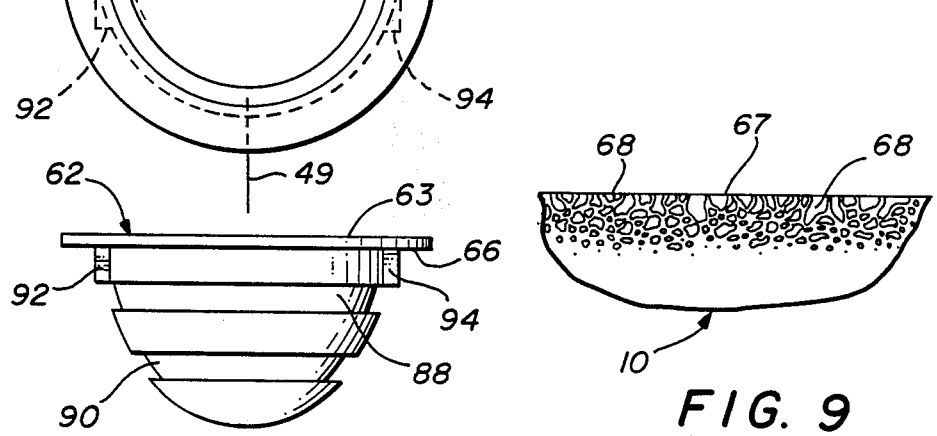
FIG. 8B
FIG. 9

METHOD AND APPARATUS FOR CEMENTING AN ACETABULAR CUP TO AN ACETABULUM

BACKGROUND OF THE INVENTION

The present invention relates to an improved method and apparatus for cementing an acetabular cup into an acetabulum.

The idea of implanting a total prosthetic device as replacement for a damaged or diseased hip joint is not a new one, having been repeated, in one form or another, numerous times since the close of the last century. It was not, however, until more recently that the total hip movement began the upward spiral of concentrated interest known today. The ability to use self curing cement such as methyl merthacrylate in orthopedics enabled the total hip concept to become a workable reality. The cement sets up within minutes at surgery and overcomes the problem of transferring weight bearing forces from the artificial device to the natural bony structures of the pelvis and femur. Even with this improvement, the present techniques of cementing an acetabular cup to the acetabulum has many problems which must be overcome.

Many acetabuli which need cup arthroplasty are irregular in shape with a somewhat flattened dome of the acetabulum. This is true because the dome in most instances has been bearing most of the weight and is the area of the greatest wear. It should be understood that while the acetabuli differ in shape corresponding to the size of the individual, the amount of water, and the like, generally speaking, an acetabulum has a deep portion forming a spherical area with a dome which is the weight bearing portion of the acetabulum and a shallow portion forming a spherical zone of larger transverse diameter than the deeper spherical area with subchondral cortical bone and some cartilage. Of course, the outer edge of the acetabulum, which is the outer edge of the spherical zone, will be irregular by virtue of the body's natural design.

One of the greater problems of cement fixation of the cup arthroplasty has been getting good fixation at the cement/bone interface. Several efforts have been made to improve this cement/bone interface. One method has used plastic spacers between the bony acetabulum and the plastic cup to allow an acceptable amount of cement to rest between the acetabulum and the cup.

A second procedure has been to surgically place drill holes in the bony acetabulum and then fill the acetabulum (and the drilled holes) with cement of a doughy consistancy. After the doughy cement has been inserted in the acetabulum, an acetabular cup is inserted into the acetabulum and manual pressure is applied to this cup to force the cement between the trabeculae of the bone and into the drill holes. Usually, three drill holes are made in the acetabulum bone so that when such holes are filled with cement and the cement hardens, the cement has greater resistance to motion. However, such drill holes create an irregular and weakened dome of the spherical zone and creates irregular pressure areas on the bony acetabulum which may lead to failure of the bone structure in those areas. Further, the doughy cement at times does not adequately penetrate the bony structure of the acetabulum because the cement is not sufficiently liquid. Also, the cement may not uniformly cover and adhere to the acetabular cup.

Still another method of attempting to improve degenerated acetabuli has been the insertion of cup arthroplasty made of plastic material such as polyethylene, sometimes a metal shell with a plastic lining and more recently a plastic inner shell with an external metal shell covered externally with the irregular porous coating. In other cases, the use of ceramic cup arthroplasty has been used. Another procedure presently advocated is the use of porous coated cup arthroplasty which is secured by placement of the porous coating next to the reamed acetabulum or the use of methyl merthacrylate to cement the cup arthroplasty into place.

Still another procedure is to insert in the acetabulum a metal cup which is free to move. This method provided minimal or no additional support to the acetabular strength or durability. Further, with the use of the porous coated arthroplasty fixation by the body's reaction, repair does not always result in solid fixation.

In some cases, an injection of liquid methyl merthacrylate is injected into the holes drilled in the wall of the acetabulum to add strength to the medullary and to add greater resistance to the slipping of the hardened methyl merthacrylate.

Other surgeons employ an impacting procedure to force the methyl merthacrylate into the acetabulum. After a sufficient amount of the doughy methyl merthacrylate has been placed in the acetabulum, a plunger which circumscribes the rim of the acetabulum is applied to the acetabulum and manual pressure is applied to the impacter which applies a force to the cement. The impacter is then removed and only atmospheric pressure remains. The cup is then pushed into the dough like cement and held in place manually with a rigid instrument until the cement has hardened.

Another involves an acetabular cup having large screw threads on the outer periphery and the cup is actually threaded into the cup shaped acetabulum. Because of the irregular shape of the acetabulum, the threads may not contact the bone structure evenly along the threads. The porous coating and screw thread methods, in some instances, use supplemental bone graft between the acetabulum and the prosthesis.

All of the former methods of cementing the cup arthroplasty produce an undesirable number of loosenings of the cement and/or cup. Such loosenings are often accompanied by further degeneration or fracture of the bone which is in approximation to the cement.

Further, in order to prepare the acetabulum to receive the cup arthroplasty, the acetabulum is reamed with a device which produces a socket or cavity with a surface which is essentially spherical but frequently eliptical in contour. In reaming such socket or cavity, usually a large portion of the cortical like subchrondral bone is removed thus weakening the area further in addition to the bone weakening caused by the holes drilled in the wall of the acetabulum. Thus, only the medullary bone is left to react in a repairative manner.

Where porous coated acetabular cups are used, some surgeons allege that the bone grows into the irregular surface of the porous coating. Others believe that microfractures are created at the surface of the reamed acetabulum thus creating minute pieces of bone which act as bone grafts and that as these grafts heal, an osteoid structure is developed and conforms to the irregular surface of the porous coating.

Several problems develop with this type of hip reconstruction. The body's repair of the reamed acetabulum is necessarily time consuming of six weeks or more. Further, it may be accompanied by fibrous union rather than bony union. The development of a fibrous union weakens the strength of the bony acetabulum. The large amount of fibrous union delays the development of bony union and may even result in non-union of the bone and a loosening of the porous cup arthroplasty from the adjacent bone.

The proposed invention overcomes the disadvantages of the prior art by attaching the acetabular cup in spaced relationship to the acetabulum and forcing a flowable cement into the space between them under pressure so as to force the flowable cement partially into the medullary bone of the acetabulum.

In addition, the acetabulum is prepared by using a first sized reamer to remove the cartilage from the deepest portion of the acetabulum to form a spherical area in the weight bearing portion of the acetabulum and, where possible, by using a second, larger diameter reamer to remove the cartilage from the shallow portion of the acetabulum to form another spherical zone with a greater diameter and preserving at least a portion of the subchondral cortical like bone. Thus, uniformly curved surfaces are formed including a weight bearing surface which is a spherical area. These uniformly curved surfaces are stronger structurally than curved surfaces composed of areas with multiple and varied radii.

In addition, at least one annular groove is formed at least in the spherical zone of the acetabulum about the inner surface thereof to provide added fixation of the cement to the bone. Also, other annular grooves can be formed in the spherical zone and/or the spherical area of the acetabulum. Further, annular projections are formed on the external or outer surface of the acetabular cup prosthesis. These grooves in the reamed acetabulum and the projections on the external surface of the acetabulum cup are separated by a space and when liquid or flowable cement is forced into that space under pressure, the grooves and projections are filled and covered with cement which, when it hardens, produces a greater resistance to motion or loosening since a geometric circle structurally distributes the stress throughout the circle and thereby produces a relatively larger area of resistance than multiple small structural areas.

Thus, it is an object of the present invention to prepare an acetabulum for receiving an acetabulum cup by reaming the cartilage from the deepest portion of the acetabulum to form a spherical area in the weight bearing portion of the acetabulum.

It is a further object of the present invention, where the acetabuli so allows, to use a second, larger diameter reamer to remove the cartilage from the shallow portion of the acetabulum and form a larger spherical zone while preserving at least a major portion of the subchondral cortical like bone of the spherical area and the spherical zone of the acetabulum.

It is yet another object of the present invention to provide better cement fixation between said arthroplasty cup and the acetabulum by forming at least one annular groove in at least the spherical zone of said acetabular wall as well as forming annular projections about the periphery of the arthroplasty cup so that when cement sets within the annular grooves in the acetabulum and the annular grooves formed by the annular projections on the outer periphery of the cup, added fixation of the cement to the bone and the cup is provided.

It is still another object of the present invention to position the acetabular cup in spaced relationship to the acetabulum and inject a flowable cement under pressure into the space between the cup and the acetabulum to thereby force some of the flowable cement into the annular groove and into the medullary bone thereby forming a ring of cement with cortical like bone and a ring of cement in the madullary bone thereby forming a better cement fixation between the cup and the bone.

It is also an object of the present invention to provide an acetabular retaining ring to hold the acetabular cup in the required spaced relationship from the acetabulum while the flowable cement sets. Also, the retaining ring, when cemented in place, allows for later pressurizing of cement in the medullary bone and between the bone and cup arthroplasty.

It is yet another object of the present invention to provide a pliable sleeve having an annular projection about the periphery thereof which mates with the annular groove on the inner surface of the acetabulum to cover the groove and prevent cement from entering it while the retaining ring is being cemented to the acetabulum.

It is still another object of the present invention to provide an adjustment ring for placement between the acetabulum cup and the retainer ring for enabling the cup to be properly positioned for a particular acetabulum.

SUMMARY OF THE INVENTION

Thus, the present invention relates to a method of attaching an acetabular cup to an acetabulum comprising the steps of preparing the acetabulum for receiving the cup, attaching the cup in spaced relationship with the acetabulum, filling the space between the cup and the acetabulum with flowable cement under pressure, and maintaining the pressure until the flowable cement hardens thereby retaining the cup in the acetabulum in a fixed relationship.

The invention also relates to apparatus for cementing an acetabular cup in an acetabulum and comprising means for holding the acetabular cup in spaced, substantially airtight relationship with the acetabulum, means for filling the space between the cup and the acetabulum with flowable cement under pressure whereby the flowable cement at least partially penetrates the bone of the acetabulum, and means for maintaining the pressure until the cement hardens thereby retaining the cup in the acetabulum.

BRIEF DESCRIPTION OF THE DRAWINGS

These and other objects of the present invention will be disclosed in conjunction with the specification and accompanying drawings in which:

FIG. 1A is a generalized cross-sectional view of a typical acetabulum;

FIG. 1B is a cross-sectional view of an acetabulum illustrating in dashed lines generally where the cortical like subchondral bone has been removed in the prior art preparation of the acetabulum to receive an acetabular cup;

FIG. 1C is a cross-sectional view of the acetabulum after it has been prepared according to the procedures of the prior art;

FIG. 1D is a cross-sectional view of the prepared acetabulum of the prior art illustrating the holes drilled in the base thereof and with a doughy like cement having been pressed into the acetabulum including the holes in the bottom thereof;

FIG. 1E is a cross-sectional view of the acetabulum of the prior art process in which an acetabular cup has been pressed into the doughy like cement and held manually until the cement hardens and further illustrates the voids that occur where the cement does not adhere to the bone or the acetabular cup;

FIG. 6 is a side view of a typical adjustment ring;

FIG. 7A is a top view of a pliable protective sleeve which is used to protect the grooves of the acetabulum to prevent cement from getting into the grooves during cementing of the retainer ring to the acetabulum;

FIG. 7B is a side view of the protective sleeve of FIG. 7A;

FIG. 8A is an isometric view of the acetabulum cup illustrating the annular projections thereon;

FIG. 8B is a side view of the acetabular cup;

FIG. 8C is a top view of the acetabular cup illustrating the flat surfaces on the opposed sides thereof where the drill bit can be easily inserted; and FIG. 9 is a typical cross-sectional view of the bone structure of the acetabulum illustrating the porous nature of the bone whereby the liquid cement can be forced under pressure partially into the bone.

DETAILED DESCRIPTION OF THE DRAWINGS

Figure 2A:
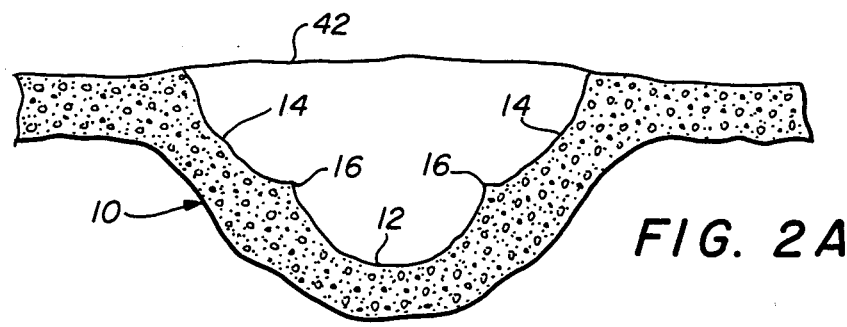
FIG. 2A is a cross-sectional view of the acetabulum after it has been prepared by the process of the present invention which leaves a spherical area and a spherical zone having a junction with greater preservation of cortical like bone and with maximum cortical like bone preserved in the spherical area and spherical zone.

While it is to be understood that acetabuli vary in shape from individual to individual depending upon the size and shape of the individual as well as the condition of the acetabulum due to wear and disease, a typical acetabulum is shown in cross-section in FIG. 1A and comprises a basic bony structure 10 having therein a deep generally spherical area 12 in the weight bearing portion of the acetabulum and a more shallow upper portion 14 being a spherical zone with a larger diameter than the spherical area 12. If the acetabulum is shallow and the head of the femur cannot seat deeply in the acetabulum then little or no spherical zone exists. When the femoral head is seated deep in the acetabulum the cartilage and subchondral bone of the spherical zone 14 may be fairly well preserved.

In order to prepare this acetabulum to receive an acetabular cup, cartilage 20 and 22 must be removed from the acetabulum by reaming.

The prior art methods of preparing the acetabulum requires reaming part of the cortical like subchondral bone 16 out of the acetabulum as shown in FIG. 1B to obtain a socket having the general shape shown by dashed lines 24.

Thus, the acetabulum shown in FIG. 1C is obtained by this reaming. It is apparent that by such reaming and removing most of the cortical like subchondral bone 16, that little cortical like bone remains and the porous medullary bone, which is weaker, is left as the supporting structure.

At this point in the prior art, as shown in FIG. 1D, holes 26 are drilled in the wall of the acetabulum and a cement 28, having a doughy like consistency, is pressed by hand or the use of a plunger like apparatus into the acetabulum to form a layer of the doughy cement 28 which also fills holes 26.

The next step of the prior art process is illustrated in FIG. 1E wherein acetabular cup 30 is forced into the acetabulum against cement 28 such that hopefully the cement 28 will fill the orifices 32 which extend in an annular manner about the periphery of the cup 30. The cup is then held stationary until the cement hardens. Because of the doughy consistency of the cement 28 and because of the uneven and perhaps irregular pressure applied to the cement 28 when the cup 30 is forced in against cement 28, voids such as shown at 34 exist wherein the cement is not touching the cup 30. In addition, if the acetabulum 10 has not been perfectly cleaned, pockets 36 of bone fragments, blood and the like are on the bottom of the acetabulum 10 and thus prevent the cement 28 from making good contact therewith. Thus, there is a possibility that the cement 28 can work loose from either the cup 30 or the acetabulum 10 creating problems for the patient.

Applicant's novel process overcomes the disadvantages of the prior art by preparing the acetabulum such that where possible the spherical area in the base of the acetabulum and the spherical zone are maintained in their generally spherical shape. It is well known that a weight bearing surface which is spherical in shape is stronger structurally than a surface comprised of multiple areas having varied radii because the stress is more uniformly distributed in a spherical structure. In addition, the acetabulum 10 is prepared such that a minimum of the cortical like subchondral bone area is removed.

Thus, as can be seen in FIG. 2A, the cartilage from spherical area 12 is removed by using a first diameter reamer thus preserving the spherical area shape. In addition, cartilage from the shallow portion of the acetabulum 10 is removed with a second larger diameter reamer thus forming a larger spherical zone 14 and preserving at least a portion 16 of the cortical like subchondral bone structure at the junction of the spherical area 12 and the spherical zone 14. Thus, not only is the thickness of the bone structure retained but the spherical shape of the weight bearing surfaces is maintained. It will be understood that with different types of acetabuli, it may not be possible to form both a spherical area 12 and a spherical zone 14 because of the shallow nature of a particular acetabulum. In that case, however, only one reamer is used to remove the cartilage from the acetabulum 10 and still maintain a basically spherical shape in the acetabulum in order to provide a better and stronger weight bearing surface.

Figure 2B:
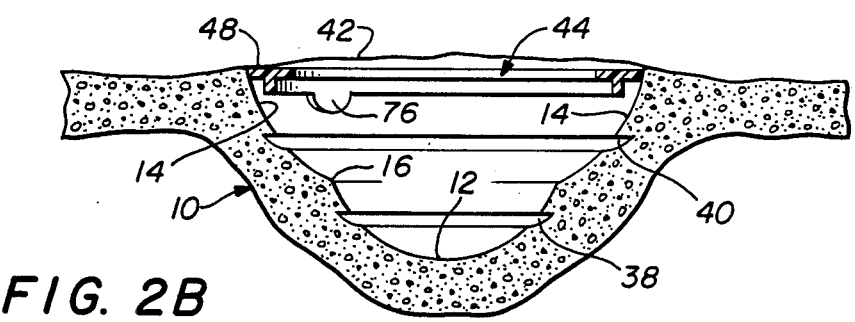
FIG. 2B illustrates the cross-sectional view of the prepared acetabulum shown in FIG. 2A and in which an annular groove has been formed in both the spherical area and the spherical zone of the acetabulum for receiving cement and in which the cup retainer ring has been properly positioned.

Next, as shown in FIG. 2B, a first annular groove 38 is formed in the spherical area 12 and a second annular groove 40 is formed in the spherical zone 14. These grooves 38 and 40 provide added fixation of the cement to the bone. Where it is not possible, because of the shape of a particular acetabulum, to form both a spherical area 12 and a spherical zone 14, then the groove 40 should be placed in the shallow portion of the acetablum 10. These annular grooves 38 and 40 are formed in a plane substantially parallel to the outer edge 42 of the spherical zone 14. Grooves 38 and 40, when filled with hardened cement, produce a greater resistance to motion or loosening since a geometric circle structurally distributes stress substantially uniformly throughout the circle and thus has a relatively larger area of resistance than multiple small depressions.

As stated earlier, because most acetabuli which need arthroplasty are eliptical in shape, one cannot usually produce a single spherical area which involves the entire acetabulum and at the same time preserve a maximum of cortical like subchondral bone 16 because as one moves from the cortical like subchondral bone 16 toward the edge of the acetabulum, one finds a spherical like zone which is that of a larger hemisphere. This larger spherical like zone should be dealt with separately with a larger reamer and attention given to completely removing the cartilage but as little cortical like subchrondral bone as possible. In reaming the spherical area 12, one should utilize the greatest portion of the acetabulum as is possible without compromise in producing a true spherical area. That portion of the acetabulum which does not lend itself to a spherical area 12 is to be dealt with as a spherical zone 14 which has, in neraly all cases, a greater radius. In most instances, a compromise will have to be made in the spherical zone area. Not all of the remaining acetabulum can be reamed into a true spherical zone. However, as large a spherical zone should be developed as is possible. The limits or size of the spherical zone is, of course, defined by the size and contour of the acetabulum as well.

When the reaming of the acetabulum is completed, there should be a spherical area 12 and a spherical zone 14 as shown in FIG. 2A. The outer edge 42 of the spherical zone 14 will be irregular by virtue of the body's natural design. However, a maximum of the cortical like subchondral bone 16 can be preserved if it is accepted that one wall of the spherical zone 14 will be wider on one side than the other. Generally, the lateral wall will be wider than the medial wall. Small irregular spots on the outer edge 42 can be smoothed in a well known manner.

Also as stated earlier, if the acetabulum is deep and of good quality, there will usually be a deep spherical area and one of the circular grooves 38 can be cut near the periphery of this area and the second circular groove 40 can be made in the spherical zone 14. If the acetabulum is extremely shallow, then the better choice is to develop one circular groove in the spherical zone area rather than to utilize any of the subchondral cortical like bone 16 of the spherical area.

When cutting the circular groove 40 in the spherical zone 14, groove 40 needs to be positioned far enough from the rim or edge 42 of the acetabulum to allow the placement of the acetabular retainer ring 44 and a small amount of cement (shown in FIG. 2C) inserted between the rim 42 of the acetabulum and the retainer ring 44 but without allowing any of the cement to enter grooves 38 and 40.

The acetabular retainer ring 44 is shown in detail in FIG. 5A, 5B, 5C, and 5D. These retainer rings 44 are of various sizes and a ring 44 of appropriate size is selected and appropriately positioned in the acetabulum 10 as shown in FIG. 2B.

Figure 2C:
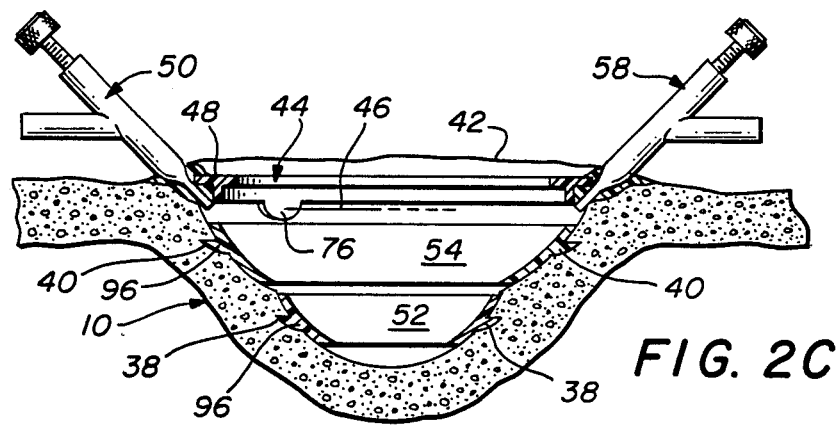
FIG. 2C further illustrates the process and apparatus of the present invention and is a cross-sectional view of the prepared acetabulum illustrating the manner in which the retaining ring is pinned to the acetabulum with a drill bit and illustrating how the cement entrance and exit tubes are constructed and inserted in spaces between the retainer ring and the acetabulum bone and cemented in place as well as showing the protective sleeves inserted within the acetabulum spherical area and spherical zone to protect the grooves and prevent cement from entering them while the retainer ring and entrance and exit cement tubes are being cemented in place.
Figure 5A:
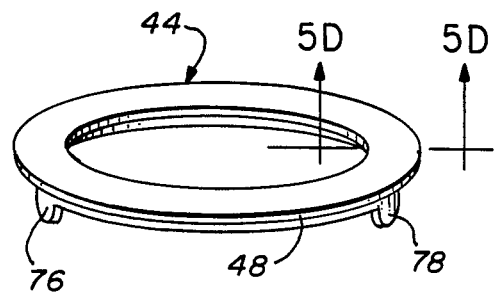
FIG. 5A is an isometric view of the retainer ring.

Upon proper positioning of the retainer ring 44 in the acetabulum 10, it is pinned with a small drill bit 46 as shown in FIG. 2C which passes through the posterolateral aspect of rim 42 of the acetabulum 10, through projection 76 of retainer ring 44, through the medial aspect of the acetabulum at a level slightly inferior to the diameter of the rim 42 of the acetabulum and through the other projection 78 shown in FIG. 5A. Thus, the maximum strength of the upper half of the bony acetabulum is preserved.

Before pinning the retainer ring 44 to the acetabulum 10, the ring 44 should be placed on the edge of the acetabulum 10 as shown in FIG. 2B to check position and gross fitting. There should be sufficient space between the outer rim 48 of retainer ring 44 and the inner edge of the acetablum 10 to insert a closeable cement introduction tube 50 (FIG. 2C) covered with silcone elastomer or othe plastic material to introduce cement into the space between the retainer ring 44 and the acetabulum 10. A pliable protective ring 52 of appropriate size and made of SILASTIC or silicone elastomer and having an annular projection 96 is placed in the circular groove 38 to prevent cement from filling the groove 38 during the time the retainer ring 44 is being cemented manually around the edges 42 of the acetabulum 10. In like manner, a larger protective sleeve 54 of appropriate size and made of silicone elastomer and having an annular projection 96 is placed in circular groove 40 to prevent cement from filling groove 40 during the time when the retainer ring 44 is being cemented manually to the outer edge 42 of the acetabulum 10.

When one is satisfied with the fitting position of the retainer ring, the retainer ring 44 is removed from the acetabulum 10 and the extreme edge 42 of the acetabulum is cleared of cartilage and soft tissue as stated earlier. A small bead of doughy methyl merthacrylate is applied to the irregular edge 42 of the acetabulum 10 or a small bead of cement is placed in the right angle corner 56 of the retainer ring 44 (shown in FIG. 5D) and the retainer is pinned with drill bit 46 as illustrated in FIG. 2C. Unfilled defects between the rim 42 of the acetabulum and the retainer ring 44 are then filled with the doughy methyl merthacrylate. Thus, a seal is formed between the outer edge of the retainer ring 44 and the adjoining portions of the acetabulum 10.

At the time the retainer ring 44 is being sealed or cemented to the rim 42 of the acetabulum 10, the cement introduction tube 50 and the cement exit tube 58 are inserted between the acetabulum 10 and the retainer ring 44 and the doughy like methyl merthacrylate cement is used to cement them in place.

Figure 2D:
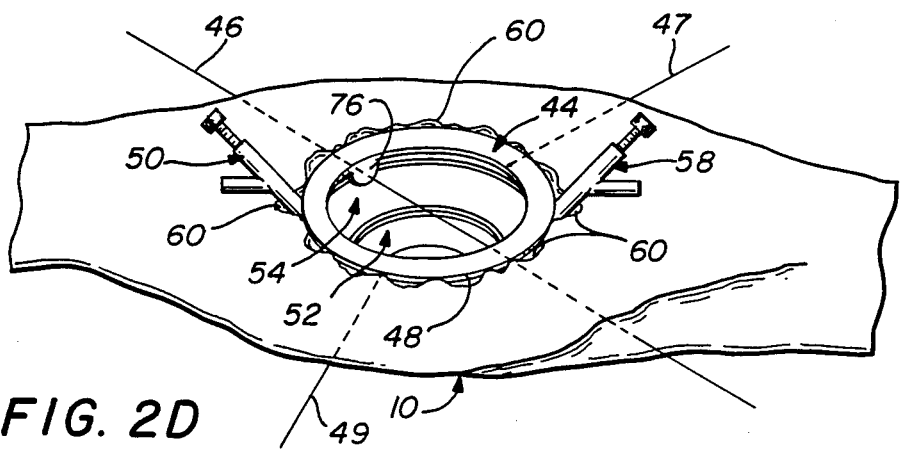
FIG. 2D is an isometric view of the retainer ring pinned in the proper place in the acetabulum with the cement entrance and exit tubes properly positioned before the cement is applied to the retainer ring and the tubes to cement them in place.

Thus, just prior to the cementing of the retainer ring 44 to the acetabulum 10, FIG. 2D illustrates the relationship of the retainer ring 44 which has been pinned by drill bit 46 through acetabulum 10 and also illustrates how the cement introduction tube 50 and the cement exit tube 58 are inserted into the unfilled defects 60 in the acetabulum rim which allow the cement flow into and out of the inside of the acetabulum through the cement introduction tubes 50 and exit tube 58. With the retainer ring 44 positioned as shown in FIG. 2D, the methyl merthacrylate cement of a doughy like consistency is pressed manually into the defects 60 of the acetabulum 10 all around the periphery of the retainer ring 44 thus making an airtight like seal.

Figure 2E:
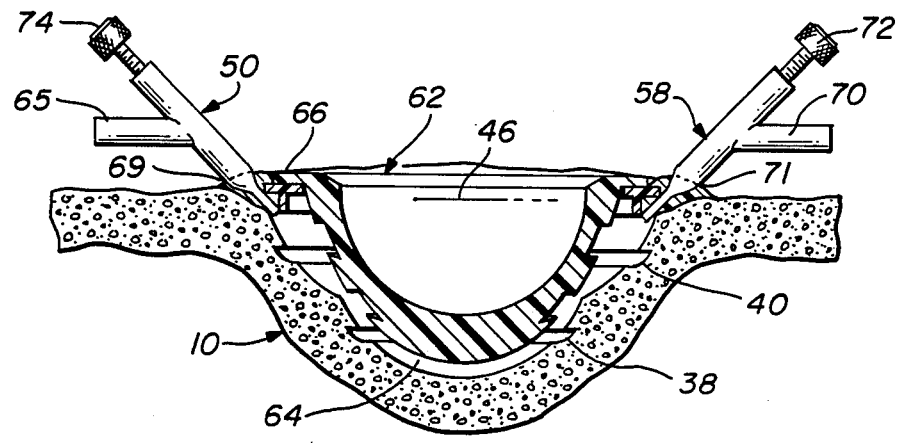
FIG. 2E is a cross-sectional view of the acetabulum with the retainer ring and entrance and exit cement tubes cemented in place and the acetabular cup being supported by the retainer ring in spaced relation with the acetabulum and ready to receive the flowable cement.

When the cement hardens, the flexible protective sleeves 52 and 54 are removed and the drill bit 46 is also removed. The acetabular cup 62 is then placed in the acetabulum and rests on the retainer ring 44. As can be seen in FIG. 8A, 8B and 8C, the acetabular cup 62 has an upper surface 63 which has a projecting ledge 66 thereon. The projecting ledge 66 rests on the upper surface of retainer ring 48 as shown in FIG. 2E.

With the acetabular cup 62 thus positioned as shown in FIG. 2E, drill bit 46 is again inserted through the acetabulum wall, the retainer ring 44 and cup 62 to hold cup 62 rigidly in place in the acetabulum 10. It will be noted that cup 62 is attached to the acetabulum 10 in spaced relationship with space 64 being available to receive a flowable cement.

Since space 64 is now nearly airtight, a flowable cement can be introduced in orifice 65 of cement introduction tube 50 under pressure to fill space 64. It will be noted that as defined herein, flowable cement means cement which will flow under pressure. This cement is thus in a liquid state and because it is in a liquid state can penetrate the porous inner surface of acetabulum 10. As can be seen in FIG. 9, the inner surface 67 of acetabulum 10 has a porous construction with openings 68 therein which can receive a liquid cement under pressure. This pressurizing of the cement in space 64 forces the liquid cement into the pores 68 of inner surface 67 of acetabulum 10 and when the cement hardens, it allows a solid connection between the cement and the bone surface 67. During the time that the liquid or flowable cement is being introduced through orifice 65 of cement introduction tube 50, cement exit tube 58 has its orifice 70 open so that any air, blood, or other liquid seepage from bone 10 may be forced out through exit tube 58 and orifice 70. When the surgeon is satisfied that sufficient air and blood have been extruded through orifice 70, and when it is determined that the cement is of sufficient viscosity to be pressurized, valve 72 of exit tube 58 can be closed which prevents any further exit of the material through orifice 70 and the pressurized cement being applied to orifice 65 forces the liquid cement into the porous bone structure of acetabulum 10. The surgeon can then close valve 74 on cement introduction tube 50 thus closing off the cement input and holding the cement in space 64 under pressure until it hardens. After the cement has hardened, the surgeon can use any well known tool to cut off the plastic input cement introduction tube 50 along line 69 next to the surface edge of cup 62 and the acetabulum 10 or may be loosened and removed. In like manner, the cement exit tube 58 can also be removed either by cutting along line 71 or by loosening and then removing tube 58.

Next, drill bit or pin 46 can be removed thus leaving the cup 62 clear of any obstacles and into which the head or ball of a matching femoral stem (not shown) can be placed for completion of the hip replacement.

Figure 5D:
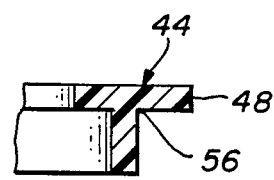
FIG. 5D is a cross-sectional view of the retainer ring of FIG. 5A illustrating the T-shaped construction.
Figure 5B:
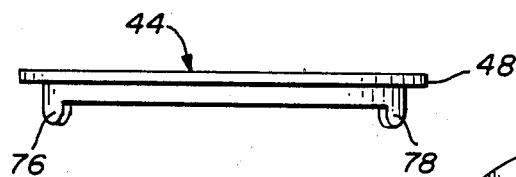
FIG. 5B is a side view of the retainer ring of FIG. 5A.
Figure 5C:
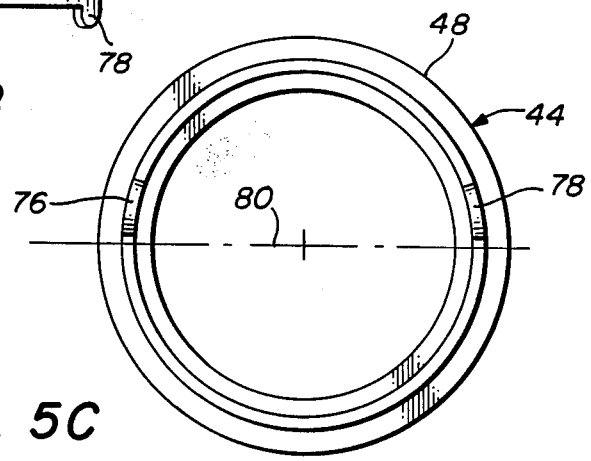
FIG. 5C is a bottom view of the retainer ring of FIG. 5A.

As can be seen in FIG. 5D, the retaining ring 44 is formed with a T-shaped cross-section. It will be noted in FIG. 5A that first and second spaced projections 76 and 78 are formed on the lower edge of the T-shaped cross-section. These projections 76 and 78 are formed in opposing relationship on the same side of and abutting a line 80 which represents the diameter of the retaining ring as shown in FIG. 5C. These projections are used for inserting the drill bit 46 as illustrated best in FIG. 2D for attaching the retainer ring 44 to the acetabulum 10. By placing the projection 76 and 78 in opposing relationship on one side of and abutting the diameter 80, the retainer ring 44 is allowed to be positioned in the acetabulum such that the drill bit 46 will not perforate the weight bearing spherical area of the acetabulum and thusly afford greater strength than if pins were placed in the weight bearing area. It will also be understood that these projections 76 and 78 could be made with flat surfaces which would be perpendicular to the entry of the drill bit 46 to prevent the drill bit 46 from sliding on the curved surface.

To hold cup 62 in a rigid relationship to acetabulum 10 in addition to the use of transverse pin 46 traversing both sides of the acetabulum 10 and both sides of the cup arthroplasty 62 it may be necessary for the surgeon to a second bit or Steinmann pin through the wall of the acetabulum 10 and into only the external surface of the cup arthroplasty 62 without penetrating the inner surface of the cup arthroplasty 62.

Alternatively, some surgeons may not wish to have pin 46 penetrate the inner surface of cup 62 as shown in FIG. 2E. If such is the case, the pin 46, pin 47 and pin 49 may be spaced about the circumference of the acetabulum 10 as shown in FIG. 2D except that the pins 46, 47 and 49 will only partially penetrate the body thickness of cup 62 as shown in FIG. 8C. The pins 46, 47 and 49 may be either plain or threaded as desired. Threaded pins will provide a more stable and secure fixation of the pins to the cup 62 and will not slip. Since the pins 46, 47 and 49 pass through the acetabulum bone and retainer ring 44, the cup 62 is held securely in place without total penetration of cup 62.

Figure 3:
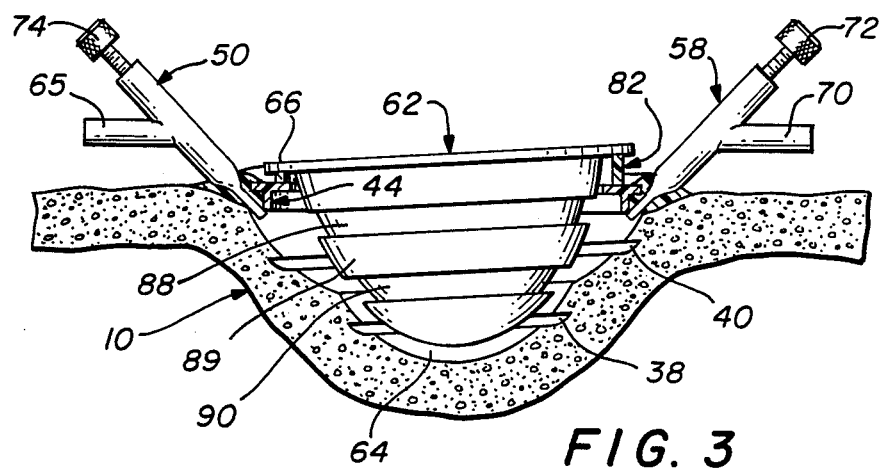
FIG. 3 is a cross-sectional view of an acetabulum having the retainer ring, the cement entrance and exit tubes and the acetabular cup in place prepared for receiving the flowable cement and illustrating how an adjustment ring can be positioned between the acetabular cup and the retainer ring to allow the acetabular cup to be located in a variety of positions to correctly fit with the acetabulum for a particular patient.
Figure 4:
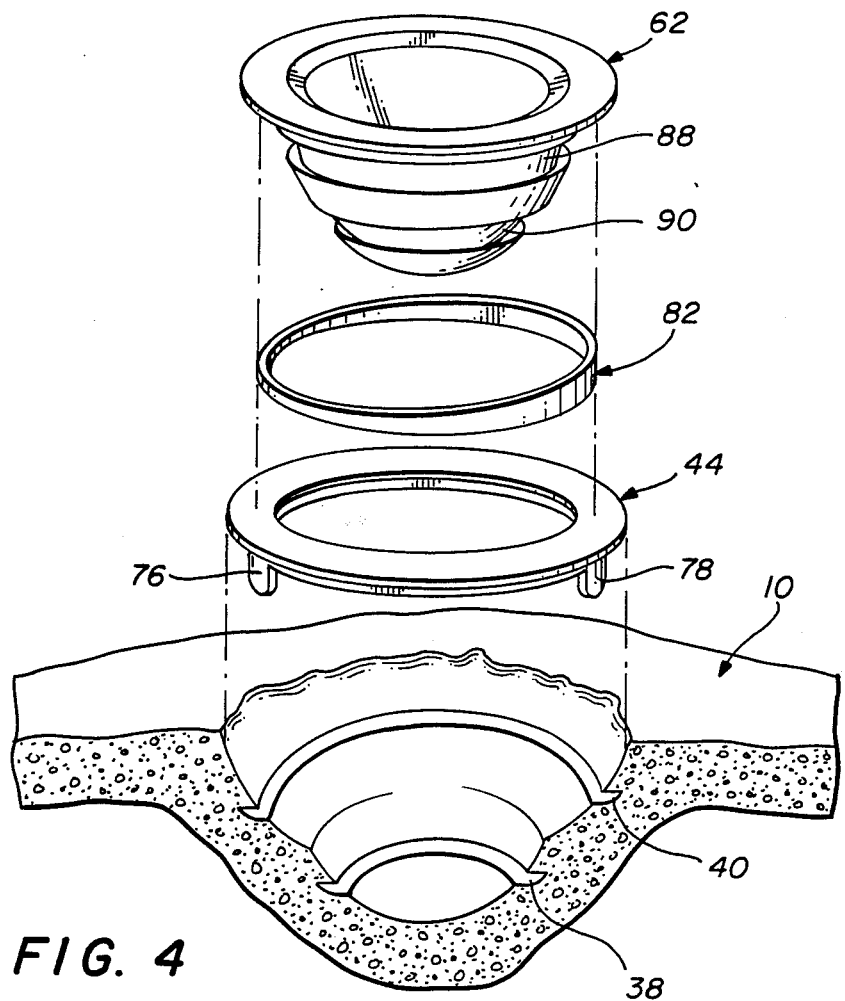
FIG. 4 is an exploded view of the acetabulum with the retainer ring, the adjustment ring and the cup illustrating how they are positioned with respect to each other.

Because the acetabuli are shaped differently for different individuals due to the physical skeletal structure of a particular individual as well as due to the wear and deterioration of the acetabulum and because the femoral prosthesis has a ball socket which must mate with the cup that is cemented in the acetabulum, it may be necessary to position the cup in the acetabulum in a particular way so as to mate properly with the femoral stem prosthesis. To that end, the present invention provides the surgeon with an adjustment sleeve 82 as shown in FIG. 3 and FIG. 6 which can be inserted between the acetabular cup 62 and the retaining ring 44. As can be seen in FIG. 4, the adjustment ring 82 is cylindrical in shape as viewed from the top with a flat bottom edge 84 and a sloping upper edge 86. The upper edge 86 is viewed as a sloping straight line from two opposing sides. It will be readily understood from observing FIG. 4 that if the adjustment ring 82 is rotated axially in its position between acetabular cup 62 and retaining ring 44, the tilted position of cup 62 with respect to acetabulum 10 will be varied.

As can be seen in FIG. 3, the adjustment ring 82 is positioned between cup 62 and retaining ring 44 and tips the cup 62 slightly to the left in FIG. 3. Thus, by rotating the positioning ring 82 about its center as viewed from the top, the tipped position of cup 62 with respect to acetabulum 10 is varied throughout the 360° rotation of the adjustment ring 82. By providing a plurality of different diameters and sizes of these adjustment rings 82 wherein they have different heights and differences in the ratio of the high side to the low side, a large number of tilted positions of cup 62 can be realized with respect to the acetabulum 10. Because the ledge 66 of cup 62 fits srugly against the upper surface of adjustment ring 82 and because the lower surface of adjustment ring 82 fits snugly against retaining ring 44 and with the use of a small amount of methyl merthacrylate about the adjustment ring and cup and retainer ring, the nearly airtight seal can be maintained when cup 62 is pinned in its final desired location so that the cement being injected into space 64 can be pressurized in a manner as described previously.

FIG. 4 is an exploded view of the assembled device shown in FIG. 3 and illustrates how cup 62 is located with respect to the upper surface of adjustment ring 82 which rests upon the upper surface of retaining ring 44 which is rigidly fixed in the upper portion of the acetabulum 10. It will be noted in FIG. 3 that annular grooves 88 and 90 are formed about the outer surface of the acetabulum cup 62 by projection 89. These grooves 88 and 90 are desirable since, when the flowable cement is introduced in the space 64 between the cup 62 and the acetabulun 10, the grooves 88 and 90 are filled with the cement and thus provide added fixation of the cup to the acetabulum in combination with grooves 38 and 40 which are cut in the surface of the acetabulum 10.

It will also be noted in FIG. 8A, 8B, and 8C that cup 62 has thereon first and second flattened surfaces 92 and 94 respectively in opposing relationship on the same side of a line 96 representing the diameter of the cup. These flattened surfaces allow the drill bit 46 to penetrate the cup more easily than is the case where the surface is curved and thus aids in preventing the drill bit 46 from slipping or migrating when the drilling begins.

It will be recalled as discussed earlier with respect to FIG. 2C, that pliable protective sleeves 52 and 54 are inserted in the acetabulum about the inner surface thereof to cover the annular grooves 38 and 40 before applying cement between the retainer ring 44 and the acetabulum 10 to prevent the cement from entering grooves 38 and 40. These pliable protective sleeves are illustrated in FIG. 7A and 7B. Since the sleeves are made of varying sizes but in the same general shape, only sleeve 38 is represented in FIG. 7A and FIG. 7B but it will be understood that the other sleeves, though of different sizes either larger or smaller are formed with the same construction. These sleeves are tapered in a frustroconical shape as shown in FIG. 7B and have an annular projection 96 about the periphery thereof which actually conforms to and mates with the grooves such as groove 38 or 40 in the acetabulum 10 thus forming a snug fit. Because of the frustral-conical shape of the pliable protective sleeve 38, it will conform to the shape of the acetabulum portion having the groove 38 or 40 therein provided that the right size is used for the particular part of the acetabulum 10 in which the groove is formed.

Thus, there has been disclosed a novel method and apparatus for cementing an acetabular cap to an acetabulum wherein the shape of the acetabulum is maintained as nearly as possible in a spherical shape to better distribute force about the weight bearing surface. In addition, the acetabular cup is rigidly attached to the acetabulum in a spaced relationship so that a liquid or flowable cement can be injected into the space under pressure to not only completely fill the space between the cup and the acetabulum but also to force the liquid like cement into the porous bone surface so as to form better adhesion between the cement and the bone. Also, annular grooves are formed about the inner periphery of the acetabulum as well as about the outer periphery of the acetabular cup so that the liquid cement will fill these grooves thus maintaining a better locking relationship of the cup to the acetabulum so that there is less chance for movement of the cup. Further, because the grooves are annular grooves, there is less likely that the cement will be torn loose from the bone structure or the cup inasmuch as weight forces are more equally distributed about an annular groove than in individual smaller recesses in various locations and furthermore by the penetration of the cement through the acetabulum annular grooves, there will be created a ring of cement in the medullary bone which will also add structural strength and stabilization. Finally, adjustment rings may be placed between the acetabular cup and the acetabulum in order to allow a cup to be positioned in a large number of positions relative to the acetabulum in order to provide a more proper fit of the femoral prosthesis head for a particular patient when it rests in the acetabular cup.

While the invention has been described in connection with a preferred embodiment, it is not intended to limit the scope of the invention to the particular form set forth, but, on the contrary, it is intended to cover such alternatives, modifications and equivalents as may be included within the spirit and scope of the invention as defined by the appended claims.

I claim:

1. A method of attaching an acetabular cup to an acetabulum comprising the steps of:
    a. preparing said acetabulum for receiving said cup,
    b. cementing a retaining ring to said acetabulum in a substantially air tight placement such that a support for said cup is formed to hold said cup in spaced relationship with said acetabulum,
    c. placing said cup in said acetabulum supported by said ring,
    d. rigidly fastening said ring and said cup to said acetabulum,
    e. filling said space between said cup and said acetabulum with flowable cement under pressure, and f. maintaining said pressure until said flowable cement hardens thereby retaining said cup in said acetabulum in a fixed relationship.

2. A method as in claim 1 wherein the step of preparing said acetabulum comprises the steps of:
   a. removing the cartilage from said acetabulum, and
   b. reaming said acetabulum to form a spherical area in the weight bearing portion of said acetabulum while preserving the subchondral cortical like bone in said acetabulum.

3. A method as in claim 1 wherein the step of preparing said acetabulum comprises the steps of:
   a. using a first diameter reamer to remove the cartilage from the deepest portion of the acetabulum and form a spherical area in the weight bearing portion of the acetabulum, and
   b. using a second larger diameter reamer to remove the cartilage from the shallow portion of said acetabulum and form a larger spherical zone while preserving at least a portion of the subchondral cortical like bone forming the spherical area and the spherical zone of the acetabulum, and
   c. smoothing rough areas of the outer edge of the spherical zone.

4. A method as in claim 1 wherein the step of filling said space between said cup and said acetabulum with cement under pressure comprises the steps of:
   a. forming a cement introduction orifice and an exit orifice coupled to said space between said cup and said acetabulum,
   b. applying flowable cement under pressure to said cement introduction orifice until said space is filled with cement and cement leaves said exit orifice, said leaving cement being of the proper consistency for correct bone penetration,
   c. closing said exit orifice, and
   d. maintaining said pressure at said cement introduction orifice until said flowable cement in said space has penetrated the porous bone structure of said acetabulum and said cement hardens.

5. A method as in claim 4 wherein the step of forming said cement introduction and exit orifices comprises the steps of:
   a. fitting and cementing said retaining ring to said acetabulum outer edge such that first and second spaces exist between said ring and the outer edge of said acetabulum,
   b. inserting a closeable cement introduction tube in said first space and a closeable cement exit tube in said second space, and
   c. cementing said cement introduction and exit tubes in place.

6. A method as in claim 5 further including the step of forming said cement introduction and exit tubes of a material that may be readily severed for removal after said cement hardens.

7. A method as in claim 5 wherein the step of preparing said acetabulum further comprises the step of forming at least one annular groove in at least said spherical zone of said acetabulum about the inner surface thereof to provide added fixation of said cement to said bone.

8. A method as in claim 7 further including the step of forming said annular groove in a plane substantially parallel to the outer edge of said spherical zone.

9. A method as in claim 8 further including the steps of:
   a. inserting a pliable protective sleeve about the inner surface of said acetabulum to cover said annular groove prior to applying cement between said ring and said acetabulum to prevent said cement for entering said groove, and
   b. removing said pliable sleeve from said acetabulum prior to inserting said acetabulum cup so that said annular groove is uncovered and ready to receive said flowable cement.

10. A method as in claim 8 further including the step of forming at least one annular groove about the outer surface of said acetabulum cup whereby when flowable cement is introduced in the space between said cup and said acetabulum, said cup groove provides added fixation of said cup to said acetabulum.

11. A method as in claim 1 wherein the step of fitting said retaining ring to said acetabulum further comprises the steps of:
   a. forming said retaining ring with a T-shaped cross-section,
   b. forming first and second spaced projections from the lower edge of said T-shaped cross-section, and
   c. pinning said retaining ring in said placement by drilling at least one bit from and through the posterior aspect of the lateral rim of the acetabulum through one of said projections, through the medial aspect of said acetabulum at a level slightly inferior to the diameter of the rim of the acetabulum, through said other projection and into the medial rim of the acetabulum.

12. A method as in claim 11 further including the step of forming said first and second retainer ring projections in opposing relationship on the same side of and abutting a line representing the diameter of said retaining ring.

13. A method as in claim 11 further including the step of forming at least first and second spaced apart flattened surfaces on the outside of said cup for entry of said drill bit during attachment of said cup to said ring to discourage said drill bit from migrating during initiating of said drilling.

14. A method as in claim 13 further including the step of forming said first and second flattened surfaces in opposing relationship on the same side of the line representing the diameter of said cup.

15. A method as in claim 1 wherein the step of attaching said cup to said retainer ring and said acetabulum further comprises the steps of:
   a. providing a plurality of adjustment rings, said rings being cylindrical in shape as viewed from the top and with a flat bottom edge and a sloping upper edge viewed as a straight line from two opposing sides,
   b. said plurality of rings having upper edges with a like plurality of different slopes,
   c. positioning various ones of said adjustment rings between said retainer ring and said acetabular cup until said cup is properly positioned for a particular acetabulum, and
   d. rigidly fixing said cup to said ring and said acetabulum in said proper position while held by said adjustment ring.

16. A method as in claim 1 wherein the step of attaching said cup to said ring and said acetabulum further comprises the steps of inserting at least one pin through said acetabulum, said retaining ring and said cup, said pin traversing both sides of said acetabulum, said retaining ring and said cup.

17. A method as in claim 1 wherein the step of attaching said cup to said ring and said acetabulum further comprises the step of inserting spaced pins through the wall of said acetabulum and said retaining ring into the external surface of said cup arthroplasty without penetrating the inner surface of said cup whereby said cup is held in rigid spaced relationship to said acetabulum.

18. A method as in claim 17 further comprising the steps of:
   a. forming screw threads on the end of each of said spaced pins, and
   b. screwing said threaded ends into said external surface of said cup whereby said pins hold said cup without slipping.

19. Appartus for cementing an acetabular cup in a acetabulum comprising:
   a. a retaining ring fitted to said acetabulum in a placement such that a support is formed to hold said cup in spaced relationship with said acetabulum, said ring being cemented in an air tight relationship with acetabulum except for a space in at least one location,
   b. means for rigidly attaching said ring and said cup to said acetabulum to hold said cup in said spaced relationship with said acetabulum,
   c. means for filling said space between said cup and said acetabulum with flowable cement under pressure whereby said flowable cement at least partially penetrates the bone of said acetabulum, and
   d. means for maintaining said pressure until said cement hardens thereby retaining said cup in said acetabulum.

20. Apparatus as in claim 19 wherein said means for filling said space between said cup and said acetabulum with flowable cement comprises a cement introducing tube inserted in a sealed relationship in said space in said one location between said ring and said acetabulum whereby flowable cement can be injected under pressure to fill said space between said cup and said acetabulum.

21. Apparatus as in claim 20 further including:
   a. a flowable cement exit orifice formed between said retainer ring and said acetabulum to allow flowable cement to exit from said space between said cup and said acetabulum, and
   b. means formed in said exit orifice for closing said exit orifice after said space between said cup and said acetabulum is filled with flowable cement thereby allowing cement to be introduced into said space under pressure.

22. Apparatus as in claim 21 wherein said means for maintaining said pressure until said cement hardens comprises means formed in said cement introducing tube to close said tube when a predetermined cement pressure has been reached thereby allowing said cement in said space between said cup and said acetabulum to harden under pressure.

23. Apparatus as in claim 22 wherein said means for rigidly attaching said ring and said cup to said acetabulum comprises at least one fastening drill bit passing through said ring, said cup and said acetabulum after said ring and cup have been properly positioned.

24. Apparatus as in claim 22 wherein said means for rigidly attaching said ring and said cup to said acetabulum comprises at least first and second pins inserted in spaced relationship through the wall of said acetabulum and said retaining ring into the external surface of said cup arthroplasty without penetrating the inner surface of said cup whereby said cup is held in rigid spaced relationship to said acetabulum.

25. Apparatus as in claim 23 wherein said cup retainer ring comprises:
   a. a T-shaped cross-section, and
   b. at least one projection extending from the lower edge of said T-shaped cross-section whereby said fastening drill bit may be inserted through said projection.

26. Apparatus as in claim 23 further including at least one flattened surface formed on the outer surface of said acetabulum cup for entry of said drill bit during attachment of said cup to said acetabulum without migration of said drill bit.

27. Apparatus as in claim 25 further including:
   a. at least one annular groove formed in said acetabulum, and
   b. at least one annular groove formed about the outer surface of said acetabulum cup whereby when flowable cement is introduced between said cup and said acetabulum, said grooves are filled with cement and provide added fixation of said cup to said acetabulum.

28. Apparatus as in claim 27 further including removable means inserted in said acetabulum to cover said annular groove and prevent cement from entering said groove during cementing of said retaining ring to said acetabulum.

29. Apparatus as in claim 27 wherein said removable means comprises:
   a. a pliable protective sleeve that conforms to the shape of said acetabulum portion having said groove, and
   b. an annular projection about the outer periphery of said sleeve, said projection conforming to and mating with said groove in said acetabulum to form a snug fit.

30. Apparatus as in claim 19 further including an adjustment ring for placement between said acetabulum cup and said retainer ring for enabling said cup to be properly positioned for a particular acetabulum.

31. Apparatus as in claim 30 wherein said adjustment ring comprises a rigid cylindrical body with a flat bottom edge and a sloping upper edge viewed as a straight line from two opposing sides whereby when said adjustment ring is axially rotated, said sloping upper edge changes position thereby varying the position of said cup with respect to said acetabulum.

32. Apparatus as in claim 31 including various sizes of said adjustment rings to allow a particular acetabular cup to be properly positioned with respect to a particular acetabulum.

33. Apparatus as in claim 32 further comprising:
   a. screw threads formed on the ends of said spaced pins, and
   b. said spaced pins being screwed into the external surface of said cup whereby said pins hold said cup without slipping.

* * * * *